US005475178A

United States Patent [19]
Del Rossi et al.

[11] Patent Number: 5,475,178
[45] Date of Patent: Dec. 12, 1995

[54] SUPPORTED HETEROPOLY ACID CATALYSTS

[75] Inventors: Kenneth J. Del Rossi, Woodbury, N.J.; Gregory A. Jablonski, Rose Valley; Charles T. Kresge, West Chester, both of Pa.; Guenter H. Kuehl, Cherry Hill, N.J.; David O. Marler, Deptford, N.J.; Gayatri S. Rav, Sewell, N.J.; Brenda H. Rose, Rosemont, Pa.

[73] Assignee: Mobil Oil Corp., Fairfax, Va.

[21] Appl. No.: 292,653

[22] Filed: Aug. 18, 1994

Related U.S. Application Data

[62] Division of Ser. No. 995,091, Dec. 22, 1992, Pat. No. 5,366,945.

[51] Int. Cl.[6] ............... C07C 2/64; C07C 15/107; C07C 2/68; C07C 5/22
[52] U.S. Cl. .............. 585/455; 585/467; 585/671; 585/654; 585/721; 585/722; 585/725; 585/732; 585/724; 585/752; 585/475; 585/481; 585/486; 585/653; 585/407; 585/640
[58] Field of Search ............... 585/455, 467, 585/671, 654, 721, 722, 725, 732, 724, 752, 475, 481, 486, 653, 407, 640

[56] References Cited

U.S. PATENT DOCUMENTS

| | | | |
|---|---|---|---|
| 3,346,657 | 10/1967 | Henke et al. | 260/671 |
| 4,146,574 | 3/1979 | Onoda et al. | 423/299 |
| 4,376,219 | 3/1983 | Murofushi et al. | 568/697 |
| 5,098,684 | 3/1992 | Kresge et al. | 423/277 |
| 5,102,643 | 4/1992 | Kresge et al. | 423/328 |
| 5,118,894 | 6/1992 | Le | 585/446 |
| 5,191,134 | 3/1993 | Le | 585/446 |
| 5,256,277 | 10/1993 | Del Rossi et al. | 208/138 |
| 5,324,881 | 6/1994 | Kresge et al. | 585/721 |

OTHER PUBLICATIONS

Ono, Y. et al., "The Catalytic Behavior of Metal Salts of Heteropolyacids in the Vapor–phase Synthesis of Methyl t–Butyl Ether," Proceedings Of The 8th International Congress Catal., vol. V., 405–416 (1984).

Nowinska, K. et al., "Catalytic Activity of Supported Heteropoly Acids for Reactions requiring Strong Acid Centres," J. Chem. Soc. Faraday Trans., 87(5), 749–753 (1991).

Matsuda, T. et al., "Effect of Pretreatment on the Acidity of Heteropoly Compounds in Butene Isomerization," J. Chem. Soc., Faraday Trans.I, 77, 3107–3117 (1981).

Nowinska, K., "Evidence for Superacid Sites on the Ammonium Salt of 12–Tungstophosphoric Acid from a Catalytic Test Reaction," J. Chem. Soc., Chem. Comm., 44–45 (1990).

Hattori, H. et al., "Solid Super Acids: Preparation and Their Catalytic Activities for Reaction of Alkanes," Journal Of Catalysis, 68, 132–143 (1981).

*Primary Examiner*—Asok Pal
*Assistant Examiner*—E. D. Irzinski
*Attorney, Agent, or Firm*—Alexander J. McKillop; Dennis P. Santini; Edward F. Kenehan, Jr.

[57] ABSTRACT

There is provided a catalyst comprising a heteropoly acid, such as phosphotungstic acid, supported on a mesoporous crystalline material, such as M41S. A particular form of this M41S support is designated as MCM-41. There is also provided a method for preparing this catalyst by impregnating the heteropoly acid on the support. There is also provided a process for using this catalyst to catalyze acid catalyzed reactions, such as the isomerization of paraffins and the alkylation of aromatics.

9 Claims, No Drawings

SUPPORTED HETEROPOLY ACID CATALYSTS

CROSS-REFERENCE TO RELATED APPLICATION

This application is a division of U.S. Application Ser. No. 07/995,091, now U.S. Pat. No. 5,366,945.

BACKGROUND

There is provided a catalyst comprising a heteropoly acid supported on a mesoporous crystalline material. There is also provided a method for preparing this catalyst. There is further provided a process for using this catalyst to catalyze acid catalyzed reactions, such as the isomerization of paraffins.

The isomerization of paraffins, especially light paraffins, is an established refining process which is traditionally used to provide additional feedstock for alkylation units or to convert relatively low octane linear paraffins to higher octane, branched chain isomers which can be blended into the gasoline pool. Straight chain paraffins such as n-butane, n-pentane and n-hexane are converted to the corresponding isoparaffins by various isomerization processes which may use various types of catalysts.

Non-regenerable Lewis and Bronsted acid catalysts may be used, for example, as disclosed in U.S. Pat. Nos. 3,766,286; 3,852,184; 3,855,346; 3,839,489; 4,144,282; and 4,814,544. Commercial processes of this type have been developed by various companies including Phillips Petroleum Company (Catalytic Isomerization) and Shell Development Company (Liquid Phase Isomerization).

An alternative type of catalyst used in a number of commercial isomerization processes comprises a metal hydrogenation/dehydrogenation component, usually platinum, on a porous support. An example of this process is the Penex process (UOP) in which the isomerization is carried out in the presence of hydrogen and a platinum catalyst. The Iso-Kel process (M. W. Kellogg) also employs a precious metal catalyst with hydrogen circulation and the Pentafining (Arco/Englehardt) and Butamer (UOP) processes also employ platinum on supports with external hydrogen circulation. Processes of this kind are disclosed, for example, in U.S. Pat. Nos. 4,834,866 (Schmidt) and 4,783,575 (Schmidt).

Isomerization processes utilizing metal components on supports comprising a molecular sieve are disclosed in U.S. Pat. Nos. 3,842,114 (Sie); 3,836,597 (Sie); 4,778,944 (Zarchy) and 4,374,296 (Haag).

Paraffin isomerization catalysts may also be employed as ring opening catalysts for the removal of cyclic aromatic precursors from reformer feedstocks as disclosed in U.S. Pat. Nos. 4,783,575 (Schmidt) and 4,834,866 (Schmidt). For example, cyclohexane, a precursor of benzene, may be isomerized to a mixture of branched paraffins which are only partly aromatized in the reformer so as to minimize the production of benzene. The utilization of paraffin isomerization for ring opening aromatic precursors, especially cyclohexane, is likely to become more important in the future as environmental regulations limit the aromatic content of motor gasoline.

SUMMARY

There is provided a catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

There is also provided a method for preparing a catalyst, said method comprising impregnating a heteropoly acid on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

There is further provided a process for converting an organic compound, said process comprising contacting said organic compound with a catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

The support material may be a non-layered material such as MCM-41.

EMBODIMENTS

Heteropoly acids are fully or partially protonated forms of oxyanions having at least one central element and at least one coordinating element Heteropoly acids may have the Keggin or Dawson structures. A particular class of heteropoly acids is the protonated form of heteropolymolybdates. These anions contain from 2 to 18 hexavalent molybdenum atoms around one or more central atoms. About 36 different elements have been identified as central atoms of these heteropolymolybdates. These anions are all highly oxygenated. Examples of heteropolymolybdates include $[PMo_{12}O_{40}]^{3-}$, $[As_2Mo_{18}O_{62}]^{6-}$, and $[TeMo_6O_{24}]^{6-}$, where the central atoms are $P^{5+}$, $As^{5+}$, and $Te^{6+}$, respectively. A more detailed discussion of heteropolymolybdates is provided in the Kirk-Othmer *Encyclopedia of Chemical Technology*, 3rd ed., 15, 688–689 (1981).

Another class of heteropoly acids, which is analogous to the protonated form of heteropolymolybdates, is the protonated form of heteropolytungstates. In heteropolytungstates, the coordinating element is tungsten instead of molybdenum.

U.S. Pat. No. 4,376,219, the entire disclosure of which is expressly incorporated herein by reference, discusses the preparation of various heteropoly acids. The central elements of these heteropoly acids may be selected from the group consisting of P, Si, B, Ge, As, Se, Ti, Zr, Mn, F, V, Ce, and Th. The coordinating elements of these heteropoly acids include Mo and/or W. Optional coordinating elements include V, Mn, Co, Ni, Cu, Zn, and Fe. The ratio of the number of the coordinating elements to the number of central elements may be from 2.5 to 12, preferably from 9 to 12. Particular heteropoly acids, which are exemplified in U.S. Pat. No. 4,376,219, include phosphotungstic acid, silicotungstic acid, 10-tungsto-2-vanadophosphoric acid, 6-tungsto-6-molybdophosphoric acid, phosphomolybdic acid, silicomolybdic acid, germanotungstic acid, tungstofluoric acid, and 18-tungsto-2-phosphoric acid. A particular heteropoly acid for use in the present catalyst is phosphotungstic acid, i.e., $H_3PW_{12}O_{40}$.

The support material for the present catalyst may be a material designated as M41S. M41S is an inorganic, non-layered, porous crystalline phase material having pores with diameters of at least about 13 Angstroms and which exhibits, after calcination, an X-ray diffraction pattern with at least one d-spacing greater than about 18 Angstroms with a relative intensity of 100. M41S is a mesoporous class of materials which are described in U.S. Pat. No. 5,102,643, the entire disclosure of which is expressly incorporated herein by reference.

A particular class of M41S materials is the class of materials designated as MCM-41. MCM-41 has a hexagonal electron diffraction pattern that can be indexed with a $d_{100}$ value greater than about 18 Angstroms and a hexagonal arrangement of uniformly sized pores with a maximum perpendicular cross section of at least about 13 Angstroms. MCM-41 materials are described in U.S. Pat. No. 5,098,684, the entire disclosure of which is expressly incorporated herein by reference.

The amount of heteropoly acid which is combined with the present support material should be a sufficient catalytic amount. The weight ratio of heteropoly acid to support material may be, for example, from about 1:20 to about 1:1.

The heteropoly acid may be combined with the support material in any manner which provides an intimate dispersion of the heteropoly acid, thereby increasing the effective surface area of the heteropoly acid. A preferred technique for combining these components is by impregnation of the support material with the heteropoly acid. The heteropoly acid may also be combined with the support material by an ion exchange technique. The impregnation technique may involve sorbing an aqueous solution of the heteropoly acid into the porous region of the support material followed by drying to remove water and to leave behind supported heteropoly acid.

The activation of paraffinic streams leading to isomerization requires a strong acid site. Unsupported heteropoly acids do not have sufficient surface areas to take advantage of their very strong acid sites. By utilizing supports with high surface areas, sufficient acid site distribution is achieved, and activation and isomerization of the paraffin is possible.

Heteropoly acids, supported on silica or alumina, have been utilized as catalysts for the formation of methyl tert-butyl ether [Ono, Y. et al., Proceedings of the 8th International congress catal., vol. V, 405 (1984)], and for the catalytic cracking of cumene and toluene disproportionation [Nowinska, K. et al., J. Chem. Soc., 87(5), 749 (1991)]. In addition, unsupported heteropoly acids have been utilized for the isomerization of but-1-ene and cis-but-2-ene [Matsuda, T. et al., J. of Chem. Soc., 77, 3107 (1981)]. Catalytic activity has been reported [Nowinska, supra, at 749] for the heteropoly acid $H_3PW_{12}O_{40}$, supported on silica (>38 wt. % $H_3PW_{12}O_{40}$ loading) and γ—$Al_2O_3$ (>60 wt. % $H_3PW_{12}O_{40}$ loading) for the low temperature (75° C.) isomerization of hexane. A maximum hexane conversion of 3.08 mol % has been observed for the silica supported sample. It was found [Nowinska, K., J. Chem. Soc., Chem. Comm., 44 (1990)] that the ammonium salt of $[PW_{12}O_{40}]^{3-}$ was capable of catalyzing the isomerization of n-hexane; however, the activity observed was low (8.6 mol % hexane conversion at 150° C.). Silica-alumina did not exhibit any catalytic activity for n-butane isomerization at low temperatures and no traces of butane isomers were found at 25° C. after 720 hours [Hattori, H. et al., J. Catal., 68, 132 (1981)]. It is important to note that the surface areas of all of the supports utilized in the literature were significantly less than the surface area of MCM-41.

The present catalysts are useful for the isomerization of linear low molecular weight paraffins to form branched-chain isoparaffins of higher octane rating. These isomerization catalysts are highly selective in that they produce a small amount of cracked products.

The mesoporous MCM-41 support materials may be characterized by a substantially uniform hexagonal honeycomb microstructure with uniform pores having a cell diameter greater than 13 Angstroms and typically in the range of 20 to 100 Angstroms. MCM-41 may be synthesized as a metallosilicate with Bronsted acid sites by incorporating a tetrahedrally coordinated trivalent element such as Al, Ga, B, or Fe within the silicate framework. MCM-41 may be identified by a microstructure with a uniform hexagonal arrangement of pores with diameters of at least about 13 Angstroms. After calcination it exhibits an X-ray diffraction pattern with at least one d-spacing greater than about 18 Angstroms with a relative intensity of 100 and a hexagonal electron diffraction pattern that can be indexed with a $d_{100}$ value greater than about 18 Angstroms which corresponds to at least one peak in the X-ray diffraction pattern.

The present catalyst may be used to isomerize $C_4$–$C_9$ paraffin hydrocarbons, either as pure compounds or mixtures. In refinery operations, the paraffins will normally be present in mixtures and, in addition to the $C_4$–$C_9$ materials, may contain hydrocarbons boiling outside this range; cycloparaffins and aromatics may also be present. Thus, the feed will comprise $C_4$–$C_9$ paraffins such as butane, pentane, hexane and these may be present in refinery streams such as raffinate cuts from solvent extraction units, reformer feedstock or pyrolysis gasoline from ethylene crackers. The feeds may also contain cyclic hydrocarbons, e.g., in the form of $C_6+$ naphthas; the cyclic materials in such feeds may undergo ring opening reactions in the presence of the catalyst with its associated metal component, to form paraffins which then undergo isomerization to iso-paraffins which can be separated from the cyclics by fractionation with the cyclics being recycled to extinction. In addition to pure paraffin feeds ($C_4$–$C_9$), mixed paraffin-olefin feeds containing significant levels of olefin may be utilized.

The isomerization is carried out in the presence of the catalyst, preferably in the presence of hydrogen. Reaction temperatures are suitably in the range of about 200° to 800° F. (about 93° to 425° C.); temperatures outside this range may be utilized although they are normally less preferred; temperatures from about 400° to 700° F. (about 205° to 370° F.) are typical. Pressures will normally be up to about 1000 psig (about 7,000 kPa abs.) although there is no reason why higher pressures should not be utilized. Lower pressures, in the range of about 50 to 100 psig (about 445 to 790 kPa abs.) may readily be employed and the use of relatively low pressures within this range will generally be preferred in order to permit the use of low pressure equipment. The isomerization is usually carried out in the presence of hydrogen, typically at a molar ratio relative to the feed from 0.1 to 10:1 and usually from 0.5:1 to 2:1. Space velocities are typically from 0.1 to 10 WHSV and usually from 0.5 to 5 WHSV. When an additional acidic material (Lewis acid or Bronsted acid) is included in the catalyst, lower operational temperatures may be used, favoring the isomerization over the less desired cracking reactions.

The catalyst used in the present isomerization process may comprise a heteropoly acid on a support of relatively low acidity which provides the desired degree of acidic functionality for the desired isomerization reactions while minimizing conversion to cracked products boiling outside the desired boiling range during the operation.

An optional metal component of the catalyst may be included, for example, in order to promote the desired isomerization reactions which, proceeding through unsaturated transitional species, require mediation by a hydrogenation-dehydrogenation component. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the optional noble metal hydrogenation component, when used, may be in the range 0.1 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the mesoporous support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation or cationic complex e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to convert the metal component to the oxide form and to confer the required mechanical strength on the catalyst. Prior to use the catalyst may be subjected to presulfiding.

Higher isomerization activity may be provided by the inclusion of an additional material having Lewis or Bronsted acid activity in the catalyst. For this purpose, both liquid and solid acid materials may be used: the high surface area of the mesoporous materials enables significant amounts of the added acidic material to be taken up. Examples of suitable additional acidic materials include aluminum trichloride, boron trifluoride and complexes of boron trifluoride, for example, with water, lower alcohols or esters. The maximum amount which may be added is set by the ability of the support material to sorb the added component and is readily determined by experiment.

The support material used for the catalyst is a mesoporous crystalline material which is described in detail below. When it is used in the present catalysts, the mesoporus crystalline material may be at least partly in the decationized or hydrogen form in order to provide the desired degree of acidic functionality, e.g., for isomerization reactions.

The support material used in the present catalysts includes a novel synthetic composition of matter comprising an ultra-large pore size crystalline phase. This material may be an inorganic, porous, non-layered, crystalline phase material which can be characterized (in its calcined form) by an X-ray diffraction pattern with at least one peak at a d-spacing greater than about 18 Angstroms with a relative intensity of 100 and a benzene sorption capacity of greater than 15 grams of benzene per 100 grams of the the material at 50 torr and 25° C.

The preferred form of the crystalline material is an inorganic, porous material having a hexagonal arrangement of uniformly sized pores with a maximum perpendicular cross-section pore dimension of at least about 13 Angstroms, and typically within the range of from about 13 Angstroms to about 200 Angstroms, identified as MCM-41. This material exhibits a hexagonal electron diffraction pattern that can be indexed with a $d_{100}$ value greater than about 18 Angstroms which corresponds to at least one peak in the X-ray diffraction pattern. This material and its preparation and properties are described in further detail in the aforementioned U.S. Pat. No. 5,098,684.

The inorganic mesoporous crystalline material used as the support component of the catalyst may have the following composition:

$$M_{n/q}(W_aX_bY_cZ_dO_h)$$

wherein W is a divalent element, such as a divalent first row transition metal, e.g., manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1.

A preferred embodiment of the above crystalline material is when (a+b+c) is greater than d, and h=2. A further embodiment is when a and d=0, and h=2. The present catalyst supports may be silicates, aluminosilicates, or other metallosilicates such as the boroaluminsilicates.

In the as-synthesized form, the support material may have a composition, on an anhydrous basis, expressed empirically as follows:

$$rRM_{n/q}(W_aX_bY_cZ_dO_h)$$

where R is the total organic material not included in M as an ion, and r is the coefficient for R, i.e., the number of moles or mole fraction of R.

The M and R components are associated with the material as a result of their presence during crystallization, and are easily removed or, in the case of M, replaced by post-crystallization methods described below.

To the extent desired, the original M, e.g., sodium or chloride, ions of the as-synthesized support material can be replaced in accordance with conventional ion-exchange techniques. Preferred replacing ions include metal ions, hydrogen ions, hydrogen precursor, e.g., ammonium, ions and mixtures of these ions. Replacing ions include hydrogen, rare earth metals and metals of Groups VIIA (e.g., Mn), VIIIA (e.g., Ni),IB (e.g., Cu), IVB (e.g., Sn) of the Periodic Table of the Elements and mixtures of these ions.

The crystalline (i.e., having sufficient order to provide a diffraction pattern such as, for example, by X-ray, electron or neutron diffraction, following calcination with at least one peak) mesoporous material may be characterized by its structure, which includes extremely large pore windows as well as by its high sorption capacity. The term "mesoporous" is used here to indicate crystals having uniform pores within the range of from about 13 Angstroms to about 200 Angstroms. The mesoporous materials have uniform pores within the range of from about 13 Angstroms to about 200

Angstroms, more usually from about 15 Angstroms to about 100 Angstroms. Since these pores are significantly larger than those of other crystalline materials, it is appropriate to refer to them as ultra-large pore size materials. For the purposes of this application, a working definition of "porous" is a material that adsorbs at least 1 gram of a small molecule, such as Ar, $N_2$, n-hexane or cyclohexane, per 100 grams of the solid.

The support material can be distinguished from other porous inorganic solids by the regularity of its large open pores whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. The preferred MCM-41 materials have a hexagonal arrangement of large open channels that can be synthesized with open internal diameters from about 13 Angstroms to about 200 Angstroms. The term "hexagonal" is intended to encompass not only materials that exhibit mathematically perfect hexagonal symmetry within the limits of experimental measurement but also those with significant observable deviations from that ideal state. A working definition as applied to the microstructure of MCM-41 would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as ±25% random deviation from the average repeat distance between adjacent channels still clearly give recognizable images of the present ultra-large pore materials. Comparable variations are also observed in the $d_{100}$ values from the electron diffraction patterns.

The size of the pores in the present mesoporous support materials is large enough that the spatiospecific selectivity with respect to transition state species in reactions such as cracking is minimized (Chen et al., "Shape Selective Catalysis in Industrial Applications", Chemical Industries, 36 41–61 (1989) to which reference is made for a discussion of the factors affecting shape selectivity). Diffusional limitations are also minimized as a result of the very large pores.

The most regular preparations of the present support material give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of MCM-41 in them. Other techniques to illustrate the microstructure of this material are transmission electron microscopy and electron diffraction. Properly oriented specimens of the MCM-41 material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of the MCM-41 material obtained so far have 20–40 distinct spots observable in the electron diffraction patterns. These patterns can be indexed with the hexagonal hk0 subset of unique reflections of 100, 110, 200, 210, etc., and their symmetry-related reflections.

In its calcined form, the crystalline material may be further characterized by an X-ray diffraction pattern with at least one peak at a position greater than about 18 Angstroms d-spacing (4.909° 2Θ for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g., thermal treatment. Pore blocking inorganic amorphous materials, e.g., silica, and organics may be removed by contact with acid or base or other chemical agents such that the detrital material will be removed without detrimental effect on the crystal.

More particularly, the calcined crystalline material may be characterized by an X-ray diffraction pattern with at least two peaks at positions greater than about 10 Angstroms d-spacing (8.842°Θ for Cu K-alpha radiation), at least one of which is at a position greater than about 18 Angstroms d-spacing, and no peaks at positions less than about 10 Angstroms d-spacing with relative intensity greater than about 20% of the strongest peak. Still more particularly, the X-ray diffraction pattern of the calcined support material will have no peaks at positions less than about 10 Angstroms d-spacing with relative intensity greater than about 10% of the strongest peak. In any event, at least one peak in the X-ray diffraction pattern will have a d-spacing that corresponds to the $d_{100}$ value of the electron diffraction pattern of the material.

The calcined inorganic crystalline material may also be characterized as having a pore size of about 13 Angstroms or greater as measured by physisorption measurements, described below. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The support materials that have the largest pore sizes may require more highly collimated incident X-ray beams in order to resolve the low angle peak from the transmitted incident X-ray beam.

The diffraction data were recorded by step-scanning at 0.04 degrees of 2Θ, where Θ is the Bragg angle, and a counting time of 10 seconds for each step. The interplanar spacings, d's, were calculated in Angstroms, and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75–100), s=strong (50–74), m=medium (25–49) and w=weak (0–24). The diffraction data listed as single lines may consist of multiple-overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the support material, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as described below.

The ammonium form of the catalytic material may be readily converted to the hydrogen form by thermal treatment (calcination). This thermal treatment is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

MCM-41 can be prepared by one of several methods, each with particular limitations.

A first method involves a reaction mixture having an $X_2O_3/YO_2$ mole ratio of from 0 to about 0.5, but an $Al_2O_3/SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, described below. This first method comprises preparing a reaction mixture containing sources of, for example, alkali or alkaline earth metal (M), e.g., sodium or potassium, cation if desired, one or a combination of oxides selected from the group consisting of divalent element W, e.g., cobalt, trivalent element X, e.g., aluminum, tetravalent element Y, e.g., silicon, and pentavalent element Z, e.g., phosphorus, an organic (R) directing agent, described below, and a solvent or solvent mixture, such as, for example, $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $Al_2O_3/SiO_2$ | 0 to 0.01 | 0.001 to 0.01 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/ $(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.01 to 2.0 | 0.03 to 1.0 | where e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of MCM-41. In this, as well as the following methods for synthesis of MCM-41, the $R_{2/f}O/(YO_2+WO+Z_2O_5+X_2O_3)$ ratio is important. When this ratio is less than 0.01 or greater than 2.0, impurity products tend to be synthesized at the expense of the desired crystalline material.

A second method for synthesis of MCM-41 involves a reaction mixture having an $X_2O_3/YO_2$ mole ratio of from about 0 to about 0.5, a crystallization temperature of from about 25° C. to about 250° C., preferably from about 50° C. to about 175° C., and two separate organic directing agents, i.e., the organic and additional organic directing agents, described below. This second method comprises preparing a reaction mixture containing sources of, for example, alkali or alkaline earth metal (M), e.g., sodium or potassium, cation if desired, one or a combination of oxides selected from the group consisting of divalent element W, e.g., cobalt, trivalent element X, e.g., aluminum, tetravalent element Y, e.g., silicon, and pentavalent element Z, e.g., phosphorus, a combination of organic directing agent and additional organic directing agent (R), each described below, and a solvent or solvent mixture, such as, for example, $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/ $(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.1 to 2.0 | 0.12 to 1.0 | where e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the precise value of the pH is not important for crystallization.

A third method for synthesis of MCM-41 is where X comprises aluminum and Y comprises silicon, the crystallization temperature must be from about 25° C. to about 175° C., preferably from about 50° C. to about 150° C., and an organic directing agent, described below, or, preferably a combination of that organic directing agent plus an additional organic agent, described below, is used. This third method comprises preparing a reaction mixture containing sources of, for example, alkali or alkaline earth metal (M), e.g., sodium or potassium, cation if desired, one or more sources of aluminum and/or silicon, an organic (R) directing agent, hereinafter more particularly described, and a solvent or solvent mixture, such as, for example $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $Al_2O_3/SiO_2$ | 0 to 0.5 | 0.001 to 0.5 |
| Solvent/$SiO_2$ | 1 to 1500 | 5 to 1000 |
| $OH^-/SiO_2$ | 0 to 10 | 0 to 5 |
| $(M_{2/e}O + R_{2/f}O)/$ $(SiO_2 + Al_2O_3)$ | 0.01 to 20 | 0.05 to 5 |
| $M_{2/e}O/$ $(SiO_2 + Al_2O_3)$ | 0 to 5 | 0 to 3 |
| $R_{2/f}O/$ $(SiO_2 + Al_2O_3)$ | 0.01 to 2 | 0.03 to 1 | where e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add the sources of oxides, e.g., silica and/or alumina such that the ratio of $R_{2/f}O/(SiO_2+Al_2O_3)$ is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the synthesis of MCM-41 involves the reaction mixture used for the third method, but the following specific procedure with tetraethylorthosilicate the source of silicon oxide:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_{2/f}O/SiO_2$ mole ratio is in the range of from about 0.5 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

In each of the above methods, batch crystallization of the crystalline material can be carried out under either static or agitated, e.g., stirred, conditions in a suitable reactor vessel, such as for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g., from about 5 minutes to about 14 days. The crystals are then separated from the liquid and recovered. Following the synthesis, the crystalline material should be subjected to treatment to remove part or all of any organic constituent.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

By adjusting conditions of the synthesis reaction for each method, like temperature, pH and time of reaction, etc., within the above limits, various embodiments of the MCM-41 crystalline material with a desired average pore size may be prepared. In particular, changing the pH, the temperature or the reaction time may promote formation of product crystals with different average pore size Non-limiting examples of various combinations of W, X, Y and Z contemplated for the first and second synthesis methods include:

| W | X | Y | Z |
|---|---|---|---|
| — | Al | Si | — |
| — | Al | — | P |
| — | Al | Si | P |
| Co | Al | — | P |
| Co | Al | Si | P |
| — | — | Si | — | including the combinations of W being Mg, or an element selected from the divalent first row transition metals, e.g., Mn, Co and Fe; X being B, Ga or Fe; and Y being Ge.

An organic directing agent for use in each of the above methods for synthesizing MCM-41 from the respective reaction mixtures is an ammonium or phosphonium ion of the formula $R_1R_2R_3R_4Q^+$, i.e.,

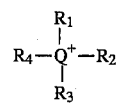

where Q is nitrogen or phosphorus and wherein at least one of $R_1$, $R_2$, $R_3$ and $R_4$ is aryl or alkyl of from 6 to about 36 carbon atoms, e.g., —$C_6H_{13}$, —$C_{10}H_{21}$, —$C_{16}H_{33}$ and —$C_{18}H_{37}$, or combinations thereof, the remainder of $R_1$, $R_2$, $R_3$ and $R_4$ being selected from hydrogen, alkyl of from 1 to 5 carbon atoms and combinations of these. The compound from which the above ammonium or phosphonium ion is derived may be, for example, the hydroxide, halide, silicate, or mixtures of these.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula wherein $R_1$, $R_2$, $R_3$ and $R_4$ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the required directing agent, when compared with other such agents known to direct synthesis of one or more other crystal structures, is believed due to its ability to form micelles which function as a template in the above reaction mixture in the nucleation and growth of the desired ultra-large pore crystals with the limitations discussed above. Non-limiting examples of these directing agents include cetyltrimethylammonium, cetyltrimethylphosphonium, cetylpyridinium, myristyltrimethylammonium, decyltrimethylammonium, dodecyltrimethylammonium and dimethyldidodecylammonium.

The reaction mixture components can be supplied by more than one source. The reaction mixture can be prepared either batchwise or continuously. Crystal size and crystallization time of M41S will vary with the nature of the reaction mixture employed and the crystallization conditions.

The crystals prepared by the synthesis procedure can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded. Normally, the crystals of the mesoporous support material will be composited with a matrix material to form the finished catalyst and for this purpose conventional matrix materials such as alumina, silica-alumina and silica are suitable with preference given to silica as a non-acidic binder. Other binder materials may be used, for example, titania, zirconia and other metal oxides or clays. The mesoporous material is usually composited with the matrix in amounts from 80:20 to 20:80 by weight, typically from 80:20 to 50:50 mesoporous material:matrix. Compositing may be done by conventional means including mulling the materials together followed by extrusion of pelletizing into the desired finished catalyst particles. A preferred method for extrusion with silica as a binder is disclosed in U.S. Pat. No. 4,582,815. If the catalyst is to be steamed in order to achieve the desired low acidity, it is performed after the catalyst has been formulated with the binder, as is conventional The catalyst may be treated by conventional pre-sulfiding treatments, e.g., by heating in the presence of hydrogen sulfide, to convert oxide forms of the metal components to their corresponding sulfides.

Although the use of the present catalyst in isomerization reactions has been emphasized hereinabove, it will be appreciated that this catalyst is useful for a variety of organic, e.g., hydrocarbon, compound conversion processes. Such conversion processes include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres a weight hourly space velocity of from about 0.5 to about 400 and a hydrogen/hydrocarbon mole ratio of from about 0 to about 20; converting alcohols, e.g. methanol, or ethers, e.g., dimethylether, or mixtures thereof to hydrocarbons including aromatics with reaction conditions including a temperature of from about 300° C. to about 550° C., more preferably from about 370° C. to about 500° C., a pressure of from about 0.01 psi to about 2000 psi, more preferably from about 0.1 psi to about 500 psi, and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating isoalkanes, e.g. isobutane, with olefins, e.g. 2-butene, with reaction conditions including a temperature of from about –25° C. to about 400° C., e.g. from about 75° C. to about 200° C., a pressure of from below atmospheric to about 5000 psig, e.g. from about atmospheric to about 1000 psig, a weight hourly space velocity based on olefin of from about 0.01 to about 100, e.g. from about 0.05 to about 20, and a mole ratio of total isoalkane to total olefin of from about 1:2 to about 1000:1, e.g. from about 3:1 to about 100:1; alkylating aromatic hydrocarbons, e.g. benzene and alkylbenzenes, in the presence of an alkylating agent, e.g., olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/ polyalkylaromatic hydrocarbon mole ratio of from about 1/1 to about 16/1; reacting olefins, e.g., isobutene or isopentene, with alcohols, e.g., methanol, to produce ethers with reaction conditions including a temperature of from about 20° C. to about 200° C., a total system pressure of from about 1 to about 200 atmospheres, an alcohol to olefin mole ratio of from about 0.1 to about 5 and a weight hourly space velocity of from 0.1 to about 200; converting light olefins, e.g., having 2 to 7 carbon atoms, to alcohol(s), ether(s) or mixtures thereof by reacting said light olefins with water under reaction conditions including a temperature from about 50° C. to about 300° C., a total pressure of at least about 5 atmospheres; and a mole ratio of water to total olefin of from about 0.1 to about 30; and transferring hydrogen from paraffins to olefins with reaction conditions including a temperature from about −25° C. to about 400° C., e.g., from about 75° C. to about 200° C., a pressure from below atmospheric to about 5000 psig, e.g., from about atmospheric to about 1000 psig, a mole ratio of total paraffin to total olefin of from about 1:2 to about 500:1, e.g., from about 5:1 to about 100:1; and a weight hourly space velocity based on olefin of from about 0.01 to about 100, e.g., from about 0.05 to about 5.

Another particular reaction for which the present catalyst may be used is the alkylation of aromatic compounds, especially with long chain alkylating agents. The term "aromatic" in reference to the alkylatable compounds is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, toluene, xylene, naphthalene, anthracene, naphthacene, perylene, coronene, phenanthrene, and alkyl-substituted derivatives of these aromatic hydrocarbons. Generally the alkyl groups which can be present as substituents on the aromatic compound contain from one to about 22 carbon atoms and preferably from about one to eight carbon atoms, and most preferably from about one to four carbon atoms..

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about C12.

Reformate containing substantial quantities of benzene, toluene and/or xylene constitutes a particularly useful feed for the aromatic alkylation process.

The alkylating agents which are useful in the aromatic alkylation process generally include any aliphatic or aromatic organic compound having one or more available alkylating aliphatic groups capable of reaction with the alkylatable aromatic compound. The alkylatable group itself may have at least about 6 carbon atoms, preferably at least about 8, and still more preferably at least about 12 carbon atoms Examples of suitable alkylating agents are olefins such as hexenes, heptenes, octenes, nonenes, decenes, undecenes, dodecenes, and the like; alcohols (inclusive of monoalcohols, dialcohols, trialcohols, etc) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylenes, etc., are also useful herein. Olefin oligomers described in U.S. Pat. No. 5,026,933 may be used as alkylating agents in the present process.

The alkylaromatic products produced by the present process are useful as synthetic lubricants. More particularly, alkylaromatic fluids have been proposed for use as certain types of functional fluids where good thermal and oxidative stability are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressier) and Pellegrini U.S. Pat. Nos. 4,211,655 and 4,238,343 describe the use of alkylaromatics as transformer oils. Properties of alkylated naphthalene lubricants are further discussed in U.S. Pat. No. 5,034,563.

Alkylated benzenes prepared by the present process are useful as synthetic lubricants and as intermediates for the preparation of detergents. More particularly, the alkylbenzenes prepared by the above-discussed alkylation process are useful as intermediates for the production of alkylphenylsulfonates, which are useful as detergents or surfactants. Processes for sulfonating alkylbenzenes are described in U.S. Pat. No. 4,298,547. More particularly, alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about −70° C. to about +60° C. Detailed descriptions of specific commercial processes abound in the literature. See, for instance, Faith, W. L. et al., INDUSTRIAL CHEMICALS, 3rd ed., 60–62 (1966). Those skilled in the field need only refer to the conventional literature for instruction on how to carry out such reactions.

The aromatic alkylation process is conducted such that the organic reactants, i.e., the alkylatable aromatic compound and the alkylating agent, are brought into contact with the catalyst composition in a suitable reaction zone such as, for example, in a flow reactor containing a fixed bed of the catalyst composition, under effective alkylation conditions. Such conditions may include a temperature of from about 0° C. to about 500° C., a pressure of from about 0.2 to about 250 atmospheres, a feed weight hourly space velocity (WHSV) of from about 0.1 $hr^{-1}$ to about 500 $hr^{-1}$ and an alkylatable aromatic compound to alkylating agent mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 50° C. to about 350° C., a pressure of from about 1 to about 25 atmospheres, a WHSV of from about 0.5 hr$^{-1}$ to about 100 hr$^{-1}$ and an alkylatable aromatic compound to alkylating agent mole ratio of from about 0.5:1 to about 5:1. The reactants can be in either the vapor phase or the liquid phase and can be neat, i.e., free from intentional admixture or dilution with other material, or they can be brought into contact with the catalyst composition with the aid of carrier gases or diluents such as, for example, hydrogen or nitrogen.

The aromatic alkylation process described herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

Another particular reaction for which the present catalyst may be used is the alkylation of isoparaffins with olefins, especially light olefins. Isoparaffin-light olefin alkylation plays an important role in the manufacture of high octane gasoline blending stocks with alkylate typically comprising 10–15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning. One measure of the selectivity of an alkylation catalyst is the $C_9+$ yield. This fraction generally results from oligomerization of the feed olefins resulting in a loss of alkylate yield, reduced alkylate quality and the possible formation of an acidic sludge fraction. The alkylation catalyst employed in the process of this invention provides reduced $C_9+$ yields relative to such known alkylation catalysts as zeolite HY, e.g., as disclosed in U.S. Pat. No. 3,865,894 referred to above.

The product produced by the isoparaffin/olefin alkylation process is of high quality based on both research and motor octane numbers and as such may be particularly well suited for blending into the gasoline pool.

The operating temperature of the isoparaffin/olefin alkylation process can extend over a fairly broad range, e.g., from about +25° to about 400° C., and is preferably within the range of from about 75° C. to about 200° C. The practical upper operating temperature will often be dictated by the need to avoid an undue occurrence of undesirable side reactions.

The pressures employed in the present isoparaffin/olefin alkylation process can extend over a considerably wide range, e.g., from subatmospheric pressure to about 5000 psig, and preferably from atmospheric pressure to about 2000 psig.

The amount of catalyst used in the present isoparaffin/olefin alkylation process can be varied over relatively wide limits. In general, the amount of catalyst as measured by the weight hourly space velocity (WHSV) based on olefin can range from about 0.01 to about 100 hr$^{-1}$, preferably from 0.04 to 5 hr$^{-1}$. It will, of course, be realized by those skilled in the art that the amount of catalyst selected for a particular reaction will be determined by several variables including the reactants involved as well as the nature of the catalyst and the operating conditions employed.

The isoparaffin reactant used in the present isoparaffin/olefin alkylation process may be one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed in the isoparaffin/olefin alkylation process generally contains from 2 to about 12 carbon atoms. Representative examples are ethylene, propylene, butene-1, butene-2, isobutylene, pentenes, hexenes, heptenes and octenes. Particularly preferred are $C_3$ and $C_4$ olefins and mixtures thereof.

In general, the mole ratio of total isoparaffin to total olefin alkylating agent in the combined hydrocarbon feed can be from about 1:2 to about 500:1 and is preferably in the range of from about 5:1 to about 100:1. The isoparaffin and/or olefin reactants can be in the vapor phase, the liquid phase and/or a supercritical state and can be neat, i.e., free from intentional admixture of dilution with other material, or the reactants can be brought into contact with the catalyst composition with the aid of carrier gases or diluents such as, for example, hydrogen or nitrogen. The reactants also may optionally be introduced to the alkylation reaction zone together with one or more other reactive materials which may serve to enhance the overall conversion operation. Thus, for example, relatively small quantities of hydrogen and/or hydrogen donors can be present in the reaction zone.

The isoparaffin/olefin alkylation process can be carried out as a batch-type, semi-continuous or continuous operation utilizing a fixed or moving bed of the catalyst component. A preferred embodiment entails use of a catalyst zone wherein the hydrocarbon charge is passed concurrently or countercurrently through a moving bed of particle-form catalyst. The latter, after use, is conducted to a regeneration zone where coke is removed, e g., by burning in an oxygen-containing atmosphere (such as air) at elevated temperature or by extracting with a solvent, after which the regenerated catalyst is recycled to the conversion zone for further contact with the organic reactants. Particular process configurations and variations may be arrived at by substituting the present catalyst for the MCM-22 catalyst as described in the U.S. Pat. Nos. 4,992,615; 5,012,033; and 5,073,665.

In the Examples which follow, the sorption data for water, cyclohexane, benzene and/or n-hexane, they are Equilibrium Adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C. The present composition exhibits an equilibrium benzene adsorption capacity at 50 Torr and 25° C. of greater than about 15 grams/100 grams, particularly greater than about 17.5 g/100 g/ and more particularly greater than about 20 g/100 g.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures.

Sorption is complete when the pressure change is not sufficient to activate the manostat.

Another way of doing this for benzene adsorption data is on a suitable thermogravimetric analysis system, such as a computer-controlled 990/951duPont TGA system. The adsorbent sample is dehydrated (physically sorbed water removed) by heating at, for example, about 350° C. or 500° C. to constant weight in flowing helium. If the sample is in as-synthesized form, e.g., containing organic directing agents, it is calcined at about 540° C. in air and held to constant weight instead of the previously described 350° C. or 500° C. treatment. Benzene adsorption isotherms are measured at 25° C. by blending a benzene saturated helium gas stream with a pure helium gas stream in the proper proportions to obtain the desired benzene partial pressure. The value of the adsorption at 50 Torr of benzene is taken from a plot of the adsorption isotherm.

In the Examples, percentages are by weight unless otherwise indicated.

EXAMPLE 1

Preparation of Support A (Highly Silicegus MCM-41)

Cab-O-Sil (50 g), 50% cetyltrimethylammonium hydroxide (CTMA-OH) (125 g) and TMA silicate (100 g) were mixed together and transferred to a 600 cc autocalve. This mixture was reacted at 100° C. for 24 hours and then at 150° C. for another 24 hours, with stirring in the autoclave. The resultant product was filtered and air dried overnight. Finally, the product was calcined at 540° C. for 1 hour in nitrogen and 6 hours in air The XRD pattern exhibits lines in the low angle region related by hexagonal symmetry consistent with the formation of MCM-41 materials. In particular the X-ray diffraction (XRD) pattern of the calcined product exhibited an intense low angle line at d=about 41 Angstroms and a broad peak at d=about 23 Angstroms. The $SiO_2/Al_2O_3$ of the resultant product is essentially infinite.

Support B (Cab-O-Sil—Amorphous silica)

Fumed silica (alumina-free Cab-O-Sil) was used as the support.

Preparation of Support C ($\gamma$-$Al_2O_3$-Alumina)

This support was prepared by co-extrusion of 33% United Catalysts $Al_2O_3$/67% Kaiser SA $Al_2O_3$. The extrudate was dried overnight at 120° C. and then calcined in dry air for 3 hours at 540° C.

Preparation of Catalysts A1, A2, A3, A4, A4D, and A5

Support A was impregnated with 5 wt. % 10 wt. %, 25 wt. %, 50 wt. % and 75 wt. % loading, respectively of $H_3PW_{12}O_{40}$ by the incipient wetness method. The samples were dried in a vacuum oven to remove the excess water. Finally, these samples were calcined at 350° C. for 1 hour in nitrogen and 4 hours in air. The calcined catalysts are designated as A1 (5 wt. %), A2 (10 wt. %), A3 (25 wt. %), A4 (50 wt. %), and A5 (75 wt. %).

Catalyst A4D was prepared by calcining A4 at 540° C. for 8 hours in air. This calcination temperature decomposes the polyanion to the $WO_3$ species.

The XRD patterns of Catalysts A1, A2, A3, A4, and A5 indicate the retention of the low angle lines due to the MCM-41 and due to the polyoxometalate. The XRD also exhibits an increase in the intensity of the peaks associated with the polyoxometalate (the broad hump at d=~11.0 Angstroms) relative to the intense peak of the MCM-41 species.

Preparation of Catalysts B1, B2, B3, B4, and B5

Support B was impregnated with 5 wt. % 10 wt. % 25 wt. % 50 wt. %, and 75 wt. % loading of the phosphotungstic acid, as described above, by the incipient wetness method. The drying and the calcination temperatures were identical to the above mentioned procedure. The calcined catalysts have been designated as B1 (5 wt. %), B2 (10 wt. %), B3 (25 wt. %), B4 (50 wt. %), and B5 (75 wt. %).

Preparation of Catalyst C5

Support C was impregnated with 75 wt. % loading of the phosphotungstic acid, by the incipient wetness technique. Drying and calcination were done as mentioned in the preparation of Catalysts A1-A5. The calcined catalyst has been designated as C5.

Preparation of Catalyst A5A

The procedure for the preparation of Catalyst A5 (75 wt. % $H_3PW_{12}O_{40}$) was repeated. This second sample of the catalyst containing 75 wt. % $H_3PW_{12}O_{40}$ is designated herein as Catalyst A5A.

Table I lists the physical properties of Support A; Catalysts A1, A2, A3, A4, A5, and A5A; Support B; Catalysts B1, B2, B3, B4, and B5; Support C; and Catalyst C5. The properties of an [A1]MCM-41 sample and an H-MCM-22 sample, which serve as reference catalysts in this disclosure, are included for comparison.

As the wt. % of the Keggin anion increases on the supports, the surface areas, benzene, n-hexane, and cyclohexane sorption capacities decrease. This is consistent with the notion that these low surface area heteropoly acids (Keggin ions) are intact and are deposited on the supports.

TABLE I

Support and Catalyst Characterization Data

| Sample | Surface Area ($m^2$/gm) | Benzene | n-$C_6$ | Cy$C_6$ | $H_2O$ | Wt. % W |
|---|---|---|---|---|---|---|
| Support A | 738 | 57.7 | 35.0 | 43.6 | 3.8 | |
| Catalyst A1 | | | 18.3 | 32.9 | 5.4 | |
| Catalyst A2 | 540 | 37.46 | 26.5 | 32.1 | 6.4 | 15.4 |
| Catalyst A3 | 518 | 36.67 | 26.5 | 31.4 | 7.9 | 15.8 |
| Catalyst A4 | 303 | 25.55 | 18.0 | 22.6 | 7.9 | 28.0 |
| Catalyst A5 | 244 | 19.43 | 15.0 | 18.7 | 10.2 | >30.0 |
| Catalyst A5A | 278 | 18.1 | 13.9 | 17.3 | 8.2 | >30.0 |
| Support B | 208 | 11.76 | 6.4 | 7.2 | 2.5 | |
| Catalyst B1 | | | 5.6 | | 3.3 | |
| Catalyst B2 | 167 | 8.48 | 4.6 | 5.1 | 5.4 | 12.8 |
| Catalyst B3 | 149 | 8.59 | 3.7 | 4.4 | 4.2 | 18.0 |
| Catalyst B4 | 107 | 5.37 | 3.1 | 3.9 | 4.7 | 27.8 |
| Catalyst B5 | 86 | 5.94 | 2.6 | 3.0 | 6.2 | >30.0 |
| Support C | 183 | 11.03 | 5.7 | 7.4 | 9.1 | |
| Catalyst $C_5$ | 56 | 4.51 | 2.0 | 2.5 | 3.6 | >30.0 |
| MCM-22 | 365 | | 13.7 | 7.6 | | |
| [Al]MCM-41 | 683 | | 23.7 | 30.5 | 38.9 | |

Preparation of Support D [Al]MCM-41

Support D was synthesized by a procedure similar to that utilized in the preparation of Support A, however, sodium aluminate was also added to achieve a $SiO_2/Al_2O_3$ of ~30. The resulting product was pelletized and precalcined for 3 hours at 425° C. in flowing $N_2$ (5 WHSV). After the precalcination, $N_2$ was shut off and air was introduced at a flow rate of 5 WHSV. Temperature was increased to 538° C. and the support was calcined for 6 hours.

After cooling to room temperature, the support was ion exchanged twice with 1N $NH_4NO_3$ solution (pH=8) for 1 hour. The ion exchanged product was filtered and dried and calcined in air at 538° C. for 3 hours.

Preparation of Catalyst D

Catalyst D was prepared by ion exchanging Support D with 0.2N ammonium nitrate, followed by exchange with $Pt(NH_3)_4Cl_2$. The catalyst was then thoroughly washed with de-ionized water, dried at 120° C., and calcined at 350° C. for 3 hours in flowing air at 5 WHSV. Table II shows physical property data for Support D and Catalyst D.

TABLE II

Support and Catalyst Characterization Data

| Sample | Surface Area | Sorption Wt. % | | | Wt. % Pt |
|---|---|---|---|---|---|
| | | N—$C_6$ | $CyC_6$ | $H_2O$ | |
| Support D | 800 | 26.4 | 30.9 | 36.9 | — |
| Catalyst D | 795 | — | — | — | 0.85 |

EXAMPLE 2 n-Butane Conversion

All experiments were performed in a fixed-bed reactor. The reactor was operated at 900 psig, at temperatures between 175° C. and 260° C., with an n-butane feed rate of 1 $hr^{-1}$ WHSV. Catalyst A5A (75 wt. % $H_3PW_{12}O_{40}$ supported on MCM-41) was pelletized and sized to 60/120 mesh. Approximately 5 g of catalyst was loaded into the reactor. The catalyst was dried for 3 hours in flowing $N_2$ (150 cc/min) at 200° C. and 900 psig. Following the drying cycle, the reactor temperature was lowered to 175° C. After thermal equilibrium was established, n-butane was fed into the reactor. Products were analyzed using a Hewlett Packard 5890 gas chromatograph with a 60 meter DB-1 column and FID detector.

The results of the conversion of n-butane over Catalyst A5A are shown in Table III. The selectivity to iso-butane (approx. 80 wt. % or greater) is significantly higher than other catalysts screened for paraffin isomerization at similar conversions (25–35 wt. %). In addition, yield losses due to high $C_3^-$ selectivities are minimized; selectivities to $C_3^-$ are less than 10 wt. %. As a comparison, ZSM-5 converted 34 wt. % n-butane at 260° C., 900 psig, and 1 WHSV, with an isobutane selectivity of 24 wt. % and a $C_3^-$ selectivity of 40 wt. %.

TABLE III n-Butane Conversion and Product Selectivities (n-butane free) as a Function of Temperature at 900 psig and 1 WHSV

| Temp, °C. | Conversion, wt. % | Selectivity, wt. % | | | | | | |
|---|---|---|---|---|---|---|---|---|
| | | $C_1$ | $C_2$ | $C_3$ | $iC_4$ | $C_4$ (total) | $C_5$ | $C_6+$ |
| 178 | 23.9 | 0.0 | 0.1 | 2.0 | 94.1 | 94.1 | 3.5 | 0.3 |
| 206 | 32.7 | 0.1 | 0.2 | 6.8 | 79.8 | 80.3 | 11.4 | 1.2 |
| 232 | 36.7 | 0.1 | 0.3 | 8.2 | 78.6 | 78.9 | 11.4 | 1.1 |
| 263 | 35.5 | 0.1 | 0.2 | 2.1 | 92.5 | 93.5 | 3.0 | 1.1 |

EXAMPLE 3 n-Hexane Conversion

N-Hexane conversion data were obtained for $H_3PW_{12}O_{40}$/MCM-41 (Catalyst A5A) and Pt/MCM-41(Catalyst D) catalysts according to the following procedure. The catalyst were pelletized and sized to 14/24 mesh. Approximately 6 g of catalyst was loaded into a ½" stainless steel fixed-bed reactor. Catalyst A5A was preheated to 175° C. at 65° C./hour, then held at 175° C. for 2 hours,. After preheating the catalyst, n-hexane was introduced at 1 WHSV with 2/1 mol/mol $H_2$/n-hexane cofeed. The total reactor effluent was analyzed with an on-line Perkin Elmer Sigma 2000 gas chromatograph equipped with a 30 meter megabore DB-1 column and FID detector.

The results of the conversion of n-hexane over Catalyst A5A and Pt/MCM-41 are shown in Table IV. The $H_3PW_{12}O_{40}$ supported on Al-free MCM-41 (A5A) was shown to be about 100° F. more active than Pt/[A1]MCM-41 and Pt/MCM-41 (highly siliceous) with comparable isoparaffin selectivities for hexane conversion. The significant activity improvement is believed to result from dispersion of heteropoly acid on the high surface MCM-41 support and not from the support itself. The n-hexane conversions and the product selectivities to isohexane and dimethyl butane are significantly higher than those reported in the literature for n-hexane conversion over an unsupported ammonium salt of $[PW_{12}O_{40}]^{3-}$ [Nowinska, K., J. Chem. Soc., Chem. Comm., 44 (1990), alumina and silica supported $H_3PW_{12}O_{40}$ [Nowinska, K. et al., J. Chem. Soc., 87(5), 749 (1991). The surface areas of the silica and alumina supports utilized in the latter study are considerably lower (159 $m^2$/g and 207 $m^2$/g, respectively) than the surface area of the MCM-41 support (738 $m^2$/g).

TABLE IV n-Hexane Conversion and Product Selectivities as a Function of Temperature, 100 psig and 1 WHSV, 2/1 mol/mol $H_2$/n-hexane Co-feed Over Catalyst A and B

| Catalyst | A | A | A | B | B |
|---|---|---|---|---|---|
| Temperature, °F. | 500 | 525 | 550 | 500 | 600 |
| n-Hexane Conversion, wt. % | 64.1 | 65.4 | 70.1 | 3.9 | 62.7 |
| $C_6$ Isoparaffin Yield, wt. % | 59.5 | 62.1 | 65.9 | 3.8 | 61.8 |
| Dimethylbutane Yield, wt. % | 10.1 | 10.3 | 11.7 | 0.1 | 10.3 |

EXAMPLE 4

Paraffin Alkylation

All experiments were conducted in a stirred autoclave operated in batch mode with nominal 50/1 i-butane/2-butene feed at 500 psig and 250° F. with a 0 8 olefin to catalyst ratio.

The performance of the heteropoly anion (75 wt. %) supported on MCM-41 (A5), amorphous silica (B5), and alumina (C5) is shown in Table V. The performance of unpromoted H-MCM-22 for i-butane/2-butene alkylation is also given in Table V for comparison. Under these conditions the olefin conversion activity of the heteropoly anion supported on MCM-41 (A5) is significantly greater than that of the unpromoted MCM-22. Similarly, the heteropoly anion supported on amorphous silica (B5) exhibits olefin conversion activity comparable to the zeolite. However, the alkylate quality obtained with the supported $H_3PW_{12}O_{40}$ catalysts is significantly lower. The amount of $C_8$ hydrocarbons produced by the unpromoted zeolite is greater than that of the heteropoly anion supported on amorphous silica (B5), MCM-41 (A5), and alumina (C5). The large decrease in the ratio of trimethylpentanes to dimethylhexanes in the $C_8$ hydrocarbon fraction indicates the poor quality of the alkylate produced by the supported heteropoly anion.

The influence of support on the activity and selectivity of the heteropoly anion was thus determined at the standard batch screening conditions. The greatest olefin conversion activity is observed with the heteropoly anion supported on MCM-41. The alkylate quality (T/D ratio) observed with the heteropoly anion supported on MCM-41, albeit worse compared with the unpromoted MCM-22, is better than when the heteropoly acid is supported on either amorphous silica or alumina.

To determine if the intact Keggin ion structure of $H_3PW_{12}O_{40}$ is important for alkylation, the performance of the heteropoly anion (50 wt. %) supported on MCM-41 was determined following decomposition by calcination at 540° C. The performance of the original material (A4) and the material following decomposition (A4D) is shown in Table VI. A ~16% decrease in olefin conversion activity is observed following decomposition of the Keggin ion and the alkylate quality (T/D ratio) decreased. This indicates that the intact Keggin ion structure is important for alkylation.

TABLE V

Influence of Support*

| Sample | A5 | B5 | C5 | MCM-22 |
|---|---|---|---|---|
| Support | MCM-41 | Cab-O-Sil | Alumina | |
| $H_3PW_{12}O_{40}$, wt. % | 75 | 75 | 75 | 0 |
| Olefin Conversion, % | 87 | 60 | 66 | 63 |
| Yield ($gC_5^+/g2C_4^=$) | 1.1 | 1.0 | 1.2 | 1.3 |
| Total Product Dist., wt. % | | | | |
| $C_5$–$C_7$ | 9.1 | 2.8 | 5.5 | 15.1 |
| $C_8$ | 57.2 | 69.7 | 58.8 | 78.6 |
| $C_9$ | 34.0 | 27.5 | 35.7 | 6.3 |
| $C_8$ Product Dist., wt. % | | | | |
| TMP (trimethylpentane) | 23.9 | 13.8 | 13.2 | 73.9 |
| DMH (dimethylhexane) | 35.8 | 25.3 | 28.0 | 13.3 |
| Unknown | 40.3 | 60.9 | 58.9 | 12.9 |
| TMP/DMH | 0.7 | 0.5 | 0.5 | 5.5 |
| TMP/($C_8$-TMP) | 0.3 | 0.2 | 0.2 | 2.8 |

*Batch autoclave screening
50/1 i-butane/2-butene feed, 500 psig, 250° F.

TABLE VI

Decomposed Polyoxometalate*
50 wt. % $H_3PW_{12}O_{40}$

| Calcination Temp., °C. | 350 | 540 |
|---|---|---|
| Structure | Keggin Ion | Decomposed |
| Sample | A4 | A4D |
| Olefin Conversion, % | 69 | 58 |
| Yield ($gC_5^+/g2C_4^=$) | 1.4 | 0.7 |
| Total Product Dist., wt. % | | |
| $C_5$–$C_7$ | 4.2 | 7.9 |
| $C_8$ | 57.8 | 63.6 |
| $C_9^+$ | 38.0 | 28.5 |
| $C_8$ Product Dist., wt. % | | |
| TMP (trimethylpentane) | 26.8 | 8.7 |
| DMH (dimethylhexane) | 31.1 | 22.9 |
| Unknown | 42.2 | 66.8 |
| TMP/DMH | 0.9 | 0.4 |
| TMP/($C_8$-TMP) | 0.4 | 0.1 |

*Batch autoclave screening
50/1 i-butane/2-butene feed, 500 psig, 250° F.

EXAMPLE 5

Aromatic Alkylation

All experiments were conducted in a stirred autoclave operated in a batch mode with 1/1/molar benzene/tetradecene feed at 200 psig and 400° F., with catalyst/feed (g/g)=0.5, in nitrogen.

The performance of the unsupported and supported (on MCM-41 and Cab-O-Sil) heteropoly acid is shown in Table VII. The performance of silica-alumina ($SiO_2/Al_2O_3$=9.6) and the [Al]MCM-41 sample, referred to in Table I, for this aromatic alkylation application are also shown in Table VII for comparison.

TABLE VII

Benzene Alkylation with Tetradecene*

| Sample | $H_3PW_{12}O_{40}$, wt. % | Conversion, % | | Product Composition, wt. % | | | | |
|---|---|---|---|---|---|---|---|---|
| | | $C_6H_6$ | $C_{14}^=$ | Monoalk. | $C_{28}$ | Dialk. | $C_{42}$ | Trialk. |
| $H_3PW_{12}O_{40}$ | Pure | 40 | 72 | 41 | 33 | 22 | 3 | — |
| Support A | 0 | 0 | 0 | 0 | 0 | 0 | 0 | 0 |
| Catalyst A1 | 5 | 37 | 78 | 45 | 33 | 20 | 2 | 0 |
| Catalyst A2 | 10 | 51 | 85 | 53 | 11 | 28 | 0 | 8 |
| Catalyst A3 | 25 | 58 | 83 | 51 | 15 | 26 | 1 | 7 |
| Catalyst A4 | 50 | 51 | 82 | 48 | 14 | 30 | 1 | 7 |
| Catalyst A5 | 75 | 54 | 83 | 53 | 15 | 27 | 1 | 4 |
| Support B | 0 | 0 | 0 | 0 | 0 | 0 | 0 | 0 |
| Catalyst B1 | 5 | 33 | 75 | 51 | 32 | 16 | 2 | 0 |
| Catalyst B2 | 10 | 51 | 82 | 51 | 12 | 30 | 0 | 7 |
| Catalyst B3 | 25 | 51 | 82 | 49 | 19 | 26 | 1 | 4 |
| Catalyst B4 | 50 | 51 | 82 | 51 | 18 | 26 | 1 | 4 |
| Catalyst B5 | 75 | 54 | 80 | 52 | 15 | 26 | 1 | 5 |
| Silica-Alumina | 0 | 44 | 86 | 38 | 17 | 31 | 3 | 11 |
| [Al]MCM-41 | 0 | 47 | 86 | 37 | 19 | 35 | 1 | 8 |

*Batch autoclave screening
1/1 benzene/tetradecene feed, 200 psig, 400° F.

Benzene and tetradecene conversions are higher, by 34% and 16%, respectively, for the supported phosphotungstic acid, as compared to the unsupported heteropoly acid. The supported heteropoly acid also produces more monoalkylate (25%), more dialkylate (26%) and trialkylate, as compared to the unsupported heteropoly acid. It also produces less dimer (58%) and trimer (75%). The performance of the supported heteropoly acid for this application is insensitive to the nature of the two supports described here and the wt. % loading of the heteropoly acid, beyond 10%. At higher benzene conversions, the supported heteropoly acid produces more monoalkylate and less dialkylate than the two reference samples. [Mono-/Di- at 10–25% loading is 1.7–2.0 (wt/wt) compared to 1.1–1.2 for the reference catalysts.]

What is claimed is:

1. A process for converting an organic compound, said process comprising contacting an organic compound with a catalyst under sufficient conversion conditions, said catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

2. An isomerization process comprising contacting a feed comprising a $C_4$-$C_9$ linear paraffin with a catalyst under sufficient conversion conditions, said catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

3. A process according to claim 2 which is carried out at a temperature from about 200° to 800° F. and at a pressure from atmospheric to about 1000 psig.

4. A process according to claim 3 which is carried out in the presence of hydrogen at a molar ratio of from 0.1:1 to 10:1 (hydrogen:paraffin).

5. A process according to claim 2, wherein said heteropoly acid is phosphotungstic acid and wherein said support material is MCM-41.

6. An aromatic alkylation process comprising contacting an aromatic with an alkylating agent and a catalyst under sufficient alkylation conditions, said catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

7. A process according to claim 6, wherein the alkylation reaction conditions include a temperature of from about 0° C. to about 500° C., a pressure of from about 0.2 to about 250 atmospheres, an WHSV of from about 0.1 $hr^{-1}$ to 500 $hr^{-1}$, and an alkylatable aromatic compound to alkylating agent mole ratio of from about 0.1:1 to 50:1.

8. An isoparaffin/olefin alkylation process which comprises contacting an isoparaffin and an olefin with a catalyst under sufficient alkylation conditions, said catalyst comprising a heteropoly acid supported on a porous support material comprising an inorganic, porous, crystalline phase material having pores with diameters of at least about 13 Angstroms and which exhibits, after calcination, an X-ray diffraction pattern with at least one d-spacing greater than about 18 Angstroms with a relative intensity of 100.

9. A process according to claim 8, wherein the alkylation reaction temperature is from about +25° C. to about 500° C., the pressure is from below atmospheric to about 5000 psig, and the weight hourly space velocity based on olefin is from about 0.01 to 100 $hr^{-1}$.

* * * * *